(12) United States Patent
Chiavazza et al.

(10) Patent No.: US 7,687,068 B2
(45) Date of Patent: Mar. 30, 2010

(54) PARTICULATE VITAMIN COMPOSITION

(75) Inventors: Véronique Chiavazza, Caluire (FR); Eraclis Statiotis, Villette d'Anthon (FR)

(73) Assignee: Adisseo France SAS (FR)

(*) Notice: Subject to any disclaimer, the term of this patent is extended or adjusted under 35 U.S.C. 154(b) by 55 days.

(21) Appl. No.: 11/584,586

(22) Filed: Oct. 23, 2006

(65) Prior Publication Data
US 2007/0036868 A1 Feb. 15, 2007

Related U.S. Application Data

(63) Continuation of application No. 10/168,317, filed as application No. PCT/EP00/13385 on Dec. 19, 2000, now abandoned.

(30) Foreign Application Priority Data
Dec. 23, 1999 (EP) .................................. 99125694

(51) Int. Cl.
A61K 47/42 (2006.01)
(52) U.S. Cl. ...................................................... 424/439
(58) Field of Classification Search .................. None
See application file for complete search history.

(56) References Cited
U.S. PATENT DOCUMENTS
5,500,415 A 3/1996 Dollat et al.
5,767,107 A 6/1998 Chaundy et al.
5,853,761 A * 12/1998 Kumabe et al. ............. 424/484

FOREIGN PATENT DOCUMENTS
EP 0261616 A2 3/1988
EP 0285682 A1 10/1988
EP 0618001 A1 10/1994
EP 1004296 A1 5/2000

OTHER PUBLICATIONS

Yoshiki et al., "Powdered nutrient preparations containing fats, proteins, inorganic salts, vitamins, dietary fiber, carbohydrates, and gelation agents," Chemical Abstracts, vol. 119, No. 11, 119:115959n, (1993).
Database WPI, Section Ch, Week 199134, Derwent Publications Ltd., London, GB; AN 1991-248698, XP002165290 and JP 03 161448 A (Asahi Chem Ind Co Ltd), Jul. 11, 1991, Abstract.
Chemical Abstracts, vol. 118, No. 7, Feb. 15, 1993, Columbus, Ohio; Abstract No. 58490; Ishibashi, Nobuhiro et al., "Food composition containing proteins and water-soluble dietary fiber, its manufacture, and its use in preventing excessive eating," XP002165289, Abstract and JP 04 262762 A (Terumo Corp., Japan), Sep. 18, 1992.

* cited by examiner

*Primary Examiner*—Carlos A Azpuru
(74) *Attorney, Agent, or Firm*—Finnegan, Henderson, Farabow, Garrett & Dunner, LLP

(57) ABSTRACT

A particulate composition comprising (a) an oil of a vitamin, an oil containing one or more vitamins or a derivative, (b) a gelling agent of vegetable origin having a glass transition point greater than 20° C., and (c) a protein, except gelatine.

20 Claims, No Drawings

PARTICULATE VITAMIN COMPOSITION

This is a continuation of application Ser. No. 10/168,317, §371 filing date of Jun. 20, 2002, now abandoned the contents of which are incorporated by reference herein, which is a national stage filing of PCT International Application No. PCT/EP00/13385, filed on Dec. 19, 2000. This application also claims the benefit of priority to European patent application no. 99125694.2, filed on Dec. 23, 1999.

The present invention relates to a particulate vitamin composition and in particular to a particulate vitamin composition comprising a gelling agent of vegetable origin.

Vitamin compositions are known. Such compositions tend to contain a gelling agent which is necessary due to the method of preparation.

In general the gelling agent used in vitamin compositions is gelatine. Gelatine is a very successful gelling agent used in compositions, it conserves the stability with regard to light, temperature and oxidation. There is, however, a need to move away from using this gelling agent as it is of animal origin and is unacceptable in many countries.

We have developed a vitamin composition which utilises a gelling agent which is not of animal origin and which provides a vitamin composition which is as stable as the gelatine-containing composition over the normal storage period.

Accordingly, the present invention provides a particulate vitamin composition comprising (a) an oil of a vitamin or a vitamin derivative, (b) a gelling agent of vegetable origin, having a glass transition point greater than 20° C., and (c) a protein, except gelatine We have found that the vitamin composition of the present invention comprising a gelling agent of vegetable origin is as stable as the conventional gelatine-containing vitamin composition.

The particulate composition of the present invention comprises an oil of a vitamin or a derivative thereof. For the purposes of the present invention, an oil of a vitamin may also include an oil containing one or more vitamin. Suitably, the vitamin is vitamin A, $D_3$ or vitamin E. Preferably, the vitamin composition comprises vitamin A.

The vitamin may be present in the particulate composition in an amount of from 1 to 50 weight %, preferably from 20 to 40 weight %.

The particulate composition of the present invention comprises a gelling agent which is of vegetable origin. The gelling agent has a glass transition point greater than 20° C., preferably between 20 and 45° C. For the purposes of the present invention, a gelling agent is defined as a substance that binds the components of the composition together and may do so by integral mixing or by forming a coating or film around the resulting particle. Suitable gelling agents include agarose, carrageenan, a carrageenan-carob mixture, native or modified starch, native or modified cellulose, xanthan gum, arabic gum, acacia gum, gellan gum and guar gum. The preferred gelling agent is carrageenan, particularly kappa-carrageenan, modified starch and acacia gum. The gelling agent may be present in the composition in an amount of from 5 to 30 weight %, preferably from 10 to 20 weight %.

The particulate composition of the present invention comprises a protein component. The protein may be any suitable protein except gelatine. In particular, the protein is any protein not of mammal tissue. Suitable proteins for use in the particulate composition of the present invention include vegetable proteins, for example potato protein; wheat gluten proteins; soya protein; milk proteins, for example lactoglobulin and casein; and fish proteins. The preferred protein is vegetable protein and milk protein, especially the milk protein, casein. The protein may be present in the particulate composition in an amount of from 2 to 40 weight %, preferably from 5 to 25 weight %.

The particulate composition of the present invention may further comprise an inorganic carrier material. Preferably, the carrier material is insoluble in aqueous solution and has a pH greater than or equal to pH 7 in water. The carrier material is suitably a phosphate or carbonate salt. The preferred salts are Group II metal phosphates or carbonates, especially calcium and magnesium phosphates and carbonates. It is preferred that the composition comprise an inorganic carrier material. The inorganic carrier material may be present in an amount of from 0 to 60 weight %, preferably from 10 to 30 weight %.

The particulate composition optionally may further comprise a sugar. Suitably, the sugar is a short chain sugar. Any suitable short chain sugar may be used, for example a reduced sugar or polyol: glycerol, sorbitol, maltitol, xylitol, Additionally sugars such as glucose, lactose, fructose, sucrose, mannose, maltose, saccharose may be used. Where a sugar is present, the preferred sugar is glucose or lactose. Alternatively, the composition may comprise a mixture of sugars or maltodextrines in dry form or in syrup form. It is preferred that the sugar mix has a Dextrose Equivalent (DE) of at least 15. The preferred sugar mix is glucose syrup. The sugar may be present in an amount of from 0 to 40 weight %, preferably from 10 to 30 weight %.

The particulate composition may further comprise an antioxidant. Suitable antioxidants include 3-tertiary butyl-4-hydroxyanisole (BHA), 3,5-di-tertiary-4-hydroxytoluene (BHT), 6-ethoxy-1,2-dihydroxy-2,2,4-trimethylquinoline (ethoxyquine) and 2-tertiary-butyl-1,4-dihydroxybenzene. Preferably, the antioxidant is 3,5-di-tertiary-4-hydroxytoluene (BHT). The antioxidant may be present in the composition in an amount of from 0 to 15 weight %, preferably from 2 to 10 weight %.

In some cases it may be desirous to include an anti-caking agent in the composition. Compounds suitable for use as an anti-caking agent include silica and magnesium stearate. Preferably, the anti-caking agent is silica. The coating agent may be present in an amount of from 0 to 3 weight %, preferably from 0.1 to 2 weight %, especially from 2 to 4 weight %.

The particulate composition may also comprise a finite amount of water. Suitably, the water is present in an amount of less than 6 weight %, preferably less than 4 weight %.

The particulate composition may be prepared by any suitable method known to the person skilled in the art. Suitable known methods of preparation include spray-drying as disclosed for, example, in European Patent No. 0258682 herein incorporated by reference, and impregnation as disclosed, for example, in European Patent No. 0261616 herein incorporated by reference. Alternatively, the particulate composition may be prepared by using a technique as disclosed in European Patent No 0618001, herein incorporated by reference, which involves the preparation of emulsions and is hereinafter referred to as the "double emulsion method".

In particular, where the gelling agent is agarose, carrageenan, a carrageenan-carob mixture, the preferred method of preparation is the double emulsion method wherein spherical droplets of vitamin are prepared by forming a primary oil-water emulsion dispersing the vitamin oil in water containing the gelling agent. The emulsion is combined with an water-immiscible solvent, for example an oil, to create a second emulsion oil-water-oil The emulsion is then cooled below the glass transition of the gelling agent to solidify the droplets and to obtain particles. A salt solution of potassium chloride may be added in the solvent after cooling. The spherical particles may then be separated by any suitable method. Thus, according to another aspect of the present invention, there is provided a process for the preparation of a vitamin composition as herein before defined which comprises (a) a first step of preparing an aqueous solution or suspension of the gelling agent, the protein, optionally the inorganic carrier and the sugar, (b) a second step of adding an oil solution of the vitamin and optionally the antioxidant to create an oil in water emulsion, (c) a third step of adding the oil in water emulsion to a vegetable oil to create an oil-water-oil emulsion, (d) a fourth step of cooling said oil-water-oil emulsion to solidify the particles; and (e) a fifth step of recovering and drying the particles characterised in that the gelling agent is agarose, carrageenan, or a carrageenan-carob mixture.

Where the gelling agent is cellulose, starch or a gum, the preferred method of preparation is the spray drying method wherein an aqueous suspension of the gelling agent is prepared with the optional components such as the inorganic carrier and sugar. The vitamin and optional antioxidant are then added to the aqueous suspension to create an emulsion. The resulting emulsion is subjected to high pressure to reduce the droplet size. The resulting droplets are then atomised using a suitable device such as a nozzle or rotating wheel. The resulting particles are then dried. Thus, according to another aspect of the present invention, there is provided a process for the preparation of a vitamin composition as herein before defined which comprises (a) a first step of preparing an aqueous solution or suspension of a gelling agent, a protein, optionally in the presence of an inorganic carrier and the sugar, (b) a second step of adding an oil solution of a vitamin optionally in the presence of an antioxidant to create an oil in water emulsion, (c) a third step of subjecting the emulsion to high pressure, (d) a fourth step of atomising said emulsion, thereby creating droplets and (e) a fifth step of drying said droplets to produce particles characterised in that the gelling agent is modified or native starch, modified or native cellulose, xantham gum, arabic gum, acacia gum gellan gum or guar gum.

The resulting particles suitably have a size of from 50 to 800 microns, preferably from 300 to 500 microns The present invention will now be described in more detail with reference to the following examples:

Examples 1 to 10 illustrate the preparation of a vitamin composition according to the present invention using the double emulsion method of preparation. Examples 11 to 14 illustrate the preparation of a vitamin composition according to the present invention using the spray drying method of preparation.

General Methods of Preparation:

(1) Double Emulsion Method

Step (1): In a first reactor, the gelling agent was dissolved in water and, where appropriate, the inorganic carrier and/or the sugar was mixed with stirring at a speed of 2 to 3 meters per second for at least twenty minutes at a temperature of 75° C. The protein was then added to complete the aqueous suspension. After twenty minutes, the temperature was decreased to 60° C.

Step (2): In a second reactor, the vitamin was mixed with the antioxidant for ten minutes to provide an oily liquid.

Step (3): The oily liquid obtained in step (2) was then added with stirring to the aqueous suspension prepared in step (1). Stirring was continued for 10 minutes whilst maintaining a temperature of 60° C. to obtain a first emulsion of oil droplets in water.

Step (4): The emulsion obtained in step (3) was then added to an a oil to provide an oil/water/oil emulsion.

Step (5): The temperature of the mixture was then reduced to 20° C. to solidify the particles. The cooled mixture was then filtered and the solid optionally washed twice with potassium chloride. The solid was further washed with n-hexane or iso-hexane to remove excess oil. The resulting particles were then dried in a fluidised bed.

(2) Spray Drying Method

The particulate composition of the present invention was prepared using the following procedure.

Step (1): In a first reactor, the gelling agent was dissolved in water at a temperature comprised between 60° C. and 80° C. When it is appropriate, the inorganic carrier and/or the sugar was added. The protein was then added to complete the aqueous suspension. The temperature was decreased to 60° C.

Step (2): In a second reactor, the vitamin was mixed with the antioxidant for ten minutes to provide an oily liquid.

Step (3): The oily liquid obtained in step (2) was then added with stirring to the aqueous suspension prepared in step (1) to ensure the formation of a coarse emulsion of oil droplets in water.

Step (4): The size of the emulsion was then reduced in a high-pressure hormogeniser by applying a high-pressure or by recycling the slurry several times at a lower pressure.

Step (5): The fine emulsion was atomised through a nozzle or through a rotating wheel. The fine particles obtained were rapidly dried in the hot spray chamber. The gas used is nitrogen and the temperature of this gas must not exceed 160° C.

EXAMPLE 1

A particulate vitamin composition was prepared according to the double emulsion preparative method described above using the following components:

| COMPONENT | EMULSION CON-CENTRATION (%) | THEORETICAL DRY CONCENTRATION (%) | WEIGHT (grams) |
|---|---|---|---|
| carrageenan | 2.69 | 14.00 | 28 |
| casein | 1.92 | 10.00 | 20 |
| CaCO$_3$ | 9.62 | 50.00 | 100 |
| Water | 80.77 | 0.00 | 840 |
| Vitamin A | 4.04 | 21.00 | 42 |
| BHT | 0.96 | 5.00 | 10 |
| TOTAL | 100 | 100 | 1040 |

The following quantities were used in the washing process:
1.5 liter of rapeseed oil
600 ml of n-hexane The particle size of the granules obtained ranged from 50 to 800 microns with 30% in the range from 315 to 500 microns. The calculated amount vitamin in the particles which comprise in fact 1.2% water was determined to be 521 700 IU vitamin/g of particles.

The actual amount of vitamin was determined by standard spectrophotometric means.

The measured amount of vitamin was 551 000 IU vitamin/g of particles. The amount of vitamin was determined after four weeks of storage at 40° C. in a dry atmosphere. The result was 530 000 IU vitamin/g of particles equating to 96% stability. The sample was included in a vitamin aggressive premix and stored for four weeks at 20° C. and 82% relative humidity. 41% of the vitamin remained under these extremes conditions showing that the composition exhibits good stability.

EXAMPLE 2

The procedure of Example 1 was repeated increasing the amount of vitamin and without any inorganic carrier. The following amounts were used:

| COMPONENT | EMULSION CONCENTRATION (%) | THEORETICAL DRY CONCENTRATION (%) | WEIGHT (grams) |
|---|---|---|---|
| carrageenan | 2.00 | 10.00 | 20 |
| casein | 8.00 | 40.00 | 80 |
| water | 80.00 | 0.00 | 800 |
| Vitamin A | 8.00 | 40.00 | 80 |
| BHT | 2.00 | 10.00 | 20 |
| TOTAL | 100 | 100 | 1000 |

The following quantities were used in the washing process:
  1.5 liter of rapeseed oil
  900 ml of n-hexane The particle size of the granules obtained ranged from 100 to 1000 microns with 30% in the range from 315 to 630 microns.

The calculated amount vitamin in the particles which comprise in fact 5% water was determined to be 950 000 IU vitamin/g of particles. The measured amount of vitamin was 834 000 IU vitamin/g of particles. The amount of vitamin was determined after four weeks of storage at 40° C. in a dry atmosphere. The result was 800 000 IU vitamin/g of particles equating to 96% stability.

EXAMPLE 3

The procedure of Example 1 was repeated reducing inorganic carrier and including maltitol. The following amounts were used:

| COMPONENT | EMULSION CONCENTRATION (%) | THEORETICAL DRY CONCENTRATION (%) | WEIGHT (grams) |
|---|---|---|---|
| carrageenan | 2.62 | 13.02 | 28 |
| Maltitol (containing 25% of water) | 5.61 | 20.93 | 60 |
| Casein | 2.24 | 11.16 | 24 |
| CaCO₃ | 5.61 | 27.91 | 60 |
| Water | 78.50 | 00.00 | 840 |
| Vitamin A | 4.30 | 21.40 | 46 |
| BHT | 1.12 | 5.58 | 12 |
| TOTAL | 100 | 100 | 1070 |

The following quantities were used in the washing process:
  1.55 liters of rape seed oil
  600 ml of n-hexane The particle size of the granules obtained ranged from 50 to 800 microns with 30% in the range from 160 to 500 microns.

The calculated amount vitamin in the particles which comprise in fact 2.6% water was determined to be 528 300 IU vitamin/g of particles. The measured amount of vitamin was 514 170 IU vitamin/g of particles. The amount of vitamin, determined after four weeks of storage at 40° C. in a dry atmosphere, was 515 400 IU vitamin/g of particles equating to 100% stability.

EXAMPLE 4

The procedure of Example 3 was repeated replacing the maltitol with sorbitol. The following amounts were used:

| COMPONENT | EMULSION CONCENTRATION(%) | THEORETICAL DRY CONCENTRATION (%) | WEIGHT (grams) |
|---|---|---|---|
| carrageenan | 2.69 | 13.40 | 28 |
| Sorbitol (containing 30% water) | 6.73 | 23.44 | 70 |
| Caseine | 2.50 | 12.44 | 26 |
| CaCO₃ | 4.62 | 22.97 | 48 |
| water | 77.88 | 0 | 810 |
| Vitamin A | 4.42 | 22.01 | 46 |
| BHT | 1.15 | 5.74 | 12 |
| TOTAL | 100 | 100 | 1040 |

The following quantities were used in the washing process:
  1.51 liters of rape seed oil
  300 ml of isohexane The particle size of the granules obtained ranged from 50 to 800 microns with approximately 30% in the range from 160 to 500 microns.

The calculated amount vitamin in the particles which comprise in fact 2.6% water was determined to be 543 270 IU vitamin/g of particles. The measured amount of vitamin was 585 360 IU vitamin/g of particles. The amount of vitamin, determined after four weeks of storage at 40° C. in a dry atmosphere was 573 650 IU vitamin/g of particles equating to 98% stability.

EXAMPLE 5

The procedure of Example 3 was repeated replacing maltitol with a glucose syrup. The following amounts were used:

| COMPONENT | EMULSION CONCENTRATION (%) | THEORETICAL DRY CONCENTRATION (%) | WEIGHT (grams) |
|---|---|---|---|
| carrageenan | 2.69 | 12.84 | 28 |
| Glucose syrup DE: 58-63 (containing 20% water) | 5.77 | 22.02 | 60 |
| Caseine | 2.31 | 11.01 | 24 |
| CaCO₃ | 5.77 | 27.52 | 60 |
| water | 77.88 | 0 | 810 |
| Vitamin A | 4.42 | 22.10 | 46 |
| BHT | 1.15 | 5.50 | 12 |
| TOTAL | 100 | 100 | 1040 |

The following quantities were used in the washing process:
  1.51 liters of rape seed oil
  600 ml of isohexane The particle size of the granules obtained ranged from 50 to 800 microns with approximately 30% in the range from 160 to 500 microns.

The calculated amount vitamin in the particles which comprise in fact 5% water was determined to be 508 150 IU vitamin/g of particles. The measured amount of vitamin was 515 900 IU vitamin/g of particles. The amount of vitamin, determined after four weeks of storage at 40° C. in a dry atmosphere was 518 990 IU vitamin/g of particles equating to 100% stability.

EXAMPLE 6

The procedure of Example 3 was repeated replacing maltitol with maltodextxine. The following amounts were used:

| COMPONENT | EMULSION CONCENTRATION (%) | THEORETICAL DRY CONCENTRATION (%) | WEIGHT (grams) |
|---|---|---|---|
| carrageenan | 2.31 | 12 | 24 |
| maltodextrine DE: 15-18 | 5.19 | 27 | 54 |
| casein | 2.12 | 11 | 22 |
| CaCO$_3$ | 4.81 | 25 | 50 |
| water | 80.77 | 0 | 840 |
| Vitamin A | 3.85 | 20 | 40 |
| BHT | 0.96 | 5 | 10 |
| TOTAL | 100 | 100 | 1040 |

The following quantities were used in the washing process:
1.5 liters of rape seed oil
600 ml of isohexane The particle size of the granules obtained ranged from 50 to 800 microns with approximately 20% in the range from 160 to 500 microns.

The calculated amount vitamin in the particles which comprise in fact 5.5% water was determined to be 479 000 IU vitamin/g of particles. The measured amount of vitamin was 489 700 IU vitamin/g of particles. The amount of vitamin, determined after four weeks of storage at 40° C. in a dry atmosphere was 485 800 UI vitamin/g of particles, equating to 100% stability.

EXAMPLE 7

The procedure of Example 1 was repeated but using powdered dried skimmed milk which brings the proteins (caseine anslactoglobuline), the sugar (lactose) and a part of the inorganic carrier (phosphate salts). The dried milk was in water at 75° C. The carrageenan was added to the milk solution, stirring at a speed of 2 meters per second. The remaining preparation was the same as in example 1. The following amounts were used:

| COMPONENT | EMULSION CONCENTRATION (%) | THEORETICAL DRY CONCENTRATION (%) | WEIGHT (grams) |
|---|---|---|---|
| carrageenan | 2.69 | 14.00 | 28 |
| Powdered dried skimmed milk | 9.62 | 50.00 | 100 |
| CaCO$_3$ | 1.92 | 10.00 | 20 |
| Water | 80.77 | 0.00 | 840 |
| Vitamin A | 4.04 | 21.00 | 42 |
| BHT | 0.96 | 5.00 | 10 |
| TOTAL | 100 | 100 | 1040 |

The following quantities were used in the washing process:
1.5 liters of rape seed oil
600 ml of isohexane The particle size of the granules obtained ranged from 50 to 800 microns with approximately 20% in the range from 160 to 500 microns.

The calculated amount vitamin in the particles which comprise in fact 5% water was determined to be 503 000 IU vitamin/g of particles. The measured amount of vitamin was 508 800 IU vitamin/g of particles. The amount of vitamin, determined after four weeks of storage at 40° C. in a dry atmosphere was 508 000 UI vitamin/g of particles, equating to 100% stability.

EXAMPLE 8

The procedure of Example 7 was repeated without calcium carbonate. The following amounts were used:

| COMPONENT | EMULSION CONCENTRATION (%) | THEORETICAL DRY CONCENTRATION (%) | WEIGHT (grams) |
|---|---|---|---|
| carrageenan | 2.69 | 14.00 | 28 |
| Powdered dried skimmed milk | 11.54 | 60.00 | 120 |
| Water | 80.77 | 0.00 | 840 |
| Vitamin A | 4.04 | 21.00 | 42 |
| BHT | 0.96 | 5.00 | 10 |
| TOTAL | 100 | 100 | 1040 |

The following quantities were used in the washing process:
1.5 liters of rape seed oil
600 ml of isohexane The particle size of the granules obtained ranged from 50 to 800 microns with approximately 40% in the range from 160 to 500 microns.

The calculated amount vitamin in the particles which comprise in fact 4.3% water was determined to be 507 800 IU vitamin/g of particles. The measured amount of vitamin was 535 400 IU vitamin/g of particles. The amount of vitamin, determined after four weeks of storage at 40° C. in a dry atmosphere was 492 600 UI vitamin/g of particles, equating to 92% stability.

The particulate composition was incorporated into a aggressive premix and stored at 20° C. and 82% relative humidity for 4 weeks. The amount of vitamin determined after this period was 64%, indicating that the composition was very stable under these under extreme conditions.

EXAMPLE 9

The procedure of Example 7 was repeated increasing the amount of vitamin and without calcium carbonate. The following amounts were used:

| COMPONENT | EMULSION CONCENTRATION (%) | THEORETICAL DRY CONCENTRATION (%) | WEIGHT (grams) |
|---|---|---|---|
| carrageenan | 2.00 | 10.00 | 20 |
| Powdered dried skimmed milk | 8.00 | 40.00 | 80 |
| Water | 80.00 | 0.00 | 800 |
| Vitamin A | 8.00 | 40.00 | 80 |
| BHT | 2.00 | 10.00 | 20 |
| TOTAL | 100 | 100 | 1000 |

The following quantities were used in the washing process:
- 1.5 liters of rape seed oil
- 600 ml of isohexane The particle size of the granules obtained ranged from 100 to 1000 microns with 50% in the range from 160 to 500 microns.

The calculated amount vitamin in the particles which comprise in fact 5% water was determined to be 950 000 IU vitamin/g of particles. The measured amount of vitamin was 850 000 IU vitamin/g of particles.

The amount of vitamin was determined after four weeks of storage at 40° C. in a dry atmosphere. The result was 825 000 IU vitamin/g of particles equating to 97% stability.

EXAMPLE 10

The procedure of Example 1 was repeated replacing the casein protein with a potato protein. The following amounts were used:

| COMPONENT | EMULSION CONCENTRATION (%) | THEORETICAL DRY CONCENTRATION (%) | WEIGHT (grams) |
|---|---|---|---|
| carrageenan | 2.69 | 14.00 | 28 |
| glycerol | 1.44 | 7.50 | 15 |
| potato protein | 0.67 | 3.50 | 7 |
| CaCO$_3$ | 9.13 | 47.50 | 95 |
| water | 80.77 | 0.00 | 840 |
| Vitamin A | 4.23 | 22.00 | 44 |
| BHT | 1.06 | 5.50 | 11 |
| TOTAL | 100 | 100 | 1040 |

The following quantities were used in the washing process:
- 1.5 liters of rape seed oil
- 4 liters of 0.3M potassium chloride
- 600 ml of isohexane The particle size of the granules obtained ranged from 50 to 800 microns with 25% in the range from 160 to 500 microns.

The calculated amount vitamin in the particles which comprise in fact 2% water was determined to be 546 500 IU vitamin/g of particles. The measured amount of vitamin was 560 650 IU vitamin/g of particles. The amount of vitamin was determined after four weeks of storage at 40° C. in a dry atmosphere. The result was 505 000 IU vitamin/g of particles equating to 90% stability.

EXAMPLE 11

A particulate vitamin composition was prepared according to the spray drying preparative method described above, using the following components:

| COMPONENT | EMULSION CONCENTRATION (%) | THEORETICAL DRY CONCENTRATION (%) | WEIGHT (grams) |
|---|---|---|---|
| Modified starch | 8.00 | 20.00 | 80 |
| Powdered dried skimmed milk | 22.00 | 55.00 | 220 |
| water | 60.00 | 0.00 | 600 |
| Vitamin A | 8.00 | 20.00 | 80 |
| BHT | 2.00 | 5.00 | 20 |
| TOTAL | 100 | 100 | 1000 |

The calculated amount vitamin in the particles which comprise in fact 5% water was determined to be 475 000 IU vitamin/g of particles. The measured amount of vitamin was 449 600 IU vitamin/g of particles. The amount of vitamin was determined after four weeks of storage at 40° C. in a dry atmosphere. The result was 452 230 IU vitamin/g of particles equating to 100% stability.

EXAMPLE 12

The procedure of Example 11 was repeated using acacia gum as the gelling agent:

| COMPONENT | EMULSION CONCENTRATION (%) | THEORETICAL DRY CONCENTRATION (%) | WEIGHT (grams) |
|---|---|---|---|
| Acacia gum | 5.00 | 20.00 | 50 |
| Powdered dried skimmed milk | 25.00 | 55.00 | 250 |
| water | 60.00 | 0.00 | 600 |
| Vitamin A | 8.00 | 20.00 | 80 |
| BHT | 2.00 | 5.00 | 20 |
| TOTAL | 100 | 100 | 1000 |

The calculated amount vitamin in the particles which comprise in fact 5% water was determined to be 475 000 IU vitamin/g of particles. The measured amount of vitamin was 454 800 IU vitamin/g of particles. The amount of vitamin was determined after four weeks of storage at 40° C. in a dry atmosphere. The result was 445 200 IU vitamin/g of particles equating to 98% stability.

EXAMPLE 13

The following amounts were used:

| COMPONENT | EMULSION CONCENTRATION (%) | THEORETICAL DRY CONCENTRATION (%) | WEIGHT (grams) |
|---|---|---|---|
| Acacia gum | 2.7 | 14.3 | 20 |
| Sodium caseinate | 6.8 | 35.7 | 50 |
| water | 81 | 0.00 | 600 |
| Vitamin A | 7.6 | 40.00 | 56 |
| BHT | 1.9 | 10.00 | 14 |
| TOTAL | 100 | 100 | 740 |

The calculated amount vitamin in the particles which comprise in fact 4% water was determined to be 1 008 000 IU vitamin/g of particles. The measured amount of vitamin was 1 050 000 IU vitamin/g of particles.

The invention claimed is:

1. A process for the preparation of a particulate vitamin composition, wherein the particulate vitamin composition comprises
   - 1 to 50% (w/w) of an oily vitamin or an oily vitamin derivative or a mixture of oily vitamins and/or oily vitamin derivatives,
   - 5 to 30% (w/w) of at least one gelling agent of vegetable origin. having a glass transition point greater than 20° C., and being selected from agarose, carrageenan and a carrageenan-carob mixture, and
   - 2 to 40% (w/w) of at least one protein, except gelatine; and wherein the process comprises (a) preparing an aqueous solution or suspension of the gelling agent and the protein, (b) adding an oil solution of a vitamin to create an oil in water emulsion, (c) adding the oil in water emulsion to a vegetable oil to create an oil-water-oil emulsion, (d) cooling the oil-water-oil emulsion to solidify the particles, and (e) recovering and drying the particles, and wherein the aqueous solution of step (a) further comprises up to 60% (w/w) of an inorganic carrier.

2. A process as claimed in claim 1, in which the inorganic carrier is a Group II metal phosphate or carbonate salt.

3. A process for the preparation of a particulate vitamin composition, wherein the particulate vitamin composition comprises
- 1 to 50% (w/w) of an oily vitamin or an oily vitamin derivative or a mixture of oily vitamins and/or oily vitamin derivatives,
- 5 to 30% (w/w) of at least one gelling agent of vegetable origin, having a glass transition point greater than 20° C., and being selected from agarose, carrageenan and a carrageenan-carob mixture, and
- 2 to 40% (w/w) of at least one protein, except gelatine; and wherein the process comprises (a) preparing an aqueous solution or suspension of the gelling agent and the protein, (b) adding an oil solution of a vitamin to create an oil in water emulsion, (c) add the oil in water emulsion to a vegetable oil to create an oil-water-oil emulsion, (d) cooling the oil-water-oil emulsion to solidify the particles, and (e) recovering and drying the particles, and wherein step (b) further comprises the addition of up to 15% (w/w) of an antioxidant.

4. A process as claimed in claim 3, in which the vitamin is vitamin A, vitamin D3, vitamin E, or a mixture of any of vitamin A, vitamin D3 and vitamin E.

5. A process as claimed in claim 4, in which the vitamin is vitamin A.

6. A process as claimed in claim 3, in which the gelling agent is carrageenan.

7. A process as claimed in claim 3, in which the protein is selected from vegetable proteins, wheat gluten proteins, soya proteins, milk proteins and fish proteins.

8. A process as claimed in claim 7, in which the protein is a vegetable protein or a milk protein.

9. A process as claimed in claim 8, in which the protein is casein.

10. A process as claimed in claim 3, in which the particulate composition comprises water in an amount of less than 6% by weight.

11. A process as claimed in claim 3, wherein the antioxidant is selected from 3-tertiary butyl-4-hydroxyanisole (BHA), 3,5-di-tertiary-4-hydroxytoluene (BHT), 6-ethoxy-1,2-dihydroxy-2,2,4-trimethylquinoline (ethoxyquine) and 2-tertiary-butyl-1,4-dihdroxybenzene.

12. A process as claimed in claim 3, wherein the oily vitamin or oily vitamin derivative or mixture of oily vitamins and/or oily vitamin derivatives is present in an amount of 20 to 40% (w/w).

13. A process as claimed in claim 3, wherein the gelling agent is present in an amount of 10 to 20% (w/w).

14. A process as claimed in claim 3, wherein the protein is present in an amount of 5 to 25% (w/w).

15. A process as claimed in claim 1, wherein the inorganic carrier is present in an amount of 10 to 30% (w/w).

16. A process as claimed in claim 3, wherein the antioxidant is present in an amount of 2 to 10% (w/w).

17. A process as claimed in claim 1, wherein the aqueous solution of step (a) further comprises up to 40% (w/w) of a sugar or a sugar mix.

18. A process as claimed in claim 17, wherein the aqueous solution of step (a) comprises a sugar or a sugar mix selected from glycerol, sorbitol, malitol, xylitol, glucose, lactose, fructose, sucrose, mannose, maltose, saccharose, mixtures thereof, glucose syrup and maltodextrines.

19. A process as claimed in claim 3, wherein the aqueous solution of step (a) further comprises up to 40% (w/w) of a sugar or a sugar mix.

20. A process as claimed in claim 19, wherein the aqueous solution of step (a) comprises a sugar or a sugar mix selected from glycerol, sorbitol, malitol, xylitol, glucose, lactose, fructose, sucrose, mannose, maltose, saccharose, mixtures thereof, glucose syrup and maltodextrines.

* * * * *